US010973391B1

(12) United States Patent
Liu

(10) Patent No.: US 10,973,391 B1
(45) Date of Patent: Apr. 13, 2021

(54) MIXED REALITY VIEWING OF A SURGICAL PROCEDURE

(71) Applicant: James X. Liu, New York, NY (US)

(72) Inventor: James X. Liu, New York, NY (US)

(*) Notice: Subject to any disclaimer, the term of this patent is extended or adjusted under 35 U.S.C. 154(b) by 385 days.

(21) Appl. No.: 15/949,201

(22) Filed: Apr. 10, 2018

Related U.S. Application Data

(60) Provisional application No. 62/509,273, filed on May 22, 2017.

(51) Int. Cl.
A61B 1/05 (2006.01)
H04N 13/243 (2018.01)
(Continued)

(52) U.S. Cl.
CPC ........ A61B 1/0005 (2013.01); A61B 1/00009 (2013.01); A61B 1/00039 (2013.01);
(Continued)

(58) Field of Classification Search
CPC .............. A61B 1/0005; A61B 1/00009; A61B 1/00096; A61B 1/00181; A61B 1/00193; A61B 1/000045; A61B 1/0615; A61B 1/07; A61B 5/7425; A61B 5/7475; A61B 2090/364; A61B 2090/365; A61B 2090/367; A61B 2090/368; A61B 2017/00216; H04N 13/239; H04N 13/279; H04N 13/243; H04N 5/23238; G06T 19/0006
See application file for complete search history.

(56) References Cited

U.S. PATENT DOCUMENTS 4,989,581 A * 2/1991 Tamburrino ......... A61B 1/0055
600/103
5,313,306 A * 5/1994 Kuban .................. G06T 3/0018
348/65
(Continued)

FOREIGN PATENT DOCUMENTS

WO WO 01/05161 A1 1/2001
WO WO 2011/002209 A2 1/2011
(Continued)

Primary Examiner — John P Leubecker
(74) Attorney, Agent, or Firm — Thomas A. O'Rourke; Bodner & O'Rourke, LLP

(57) ABSTRACT

A system for virtual reality/mixed reality viewing of a surgical procedure includes an endoscope having an elongated flexible or rigid main body with a proximal end and a distal end. A spherical element is coupled to the distal end. A plurality of wide field-of-view cameras or optical collections lenses are aligned about the spherical element to provide 360 degree omnidirectional stereoscopic visualization. A fiber optic illumination strip is positioned around the periphery of the spherical element adjacent each camera. A central processing unit is in communication with the plurality of cameras/lenses configured to receive real-time video from each of the plurality of cameras or lenses. A partial field-of-view virtual reality headset or a mixed reality headset is electronically coupled to the central processing unit. The headset displays real-time video from a select portion of the plurality of cameras or lenses, which provides 360 degree omnidirectional visualization based upon a position of the headset.

20 Claims, 13 Drawing Sheets

(51) Int. Cl.
*H04N 13/254* (2018.01)
*H04N 13/332* (2018.01)
*H04N 13/366* (2018.01)
*A61B 1/06* (2006.01)
*A61B 1/00* (2006.01)
*A61B 1/07* (2006.01)
*G06T 19/00* (2011.01)

(52) U.S. Cl.
CPC ...... *A61B 1/00048* (2013.01); *A61B 1/00096* (2013.01); *A61B 1/00114* (2013.01); *A61B 1/00117* (2013.01); *A61B 1/00142* (2013.01); *A61B 1/00181* (2013.01); *A61B 1/00193* (2013.01); *A61B 1/051* (2013.01); *A61B 1/07* (2013.01); *H04N 13/243* (2018.05); *H04N 13/254* (2018.05); *H04N 13/332* (2018.05); *H04N 13/366* (2018.05); *A61B 1/0615* (2013.01); *G06T 19/006* (2013.01); *H04N 2213/001* (2013.01)

(56) References Cited

U.S. PATENT DOCUMENTS

| | | | | |
|---|---|---|---|---|
| 5,359,363 A * | 10/1994 | Kuban | ................. | G06T 3/0018 348/36 |
| 5,495,576 A * | 2/1996 | Ritchey | ................. | G06T 17/00 345/420 |
| 5,547,455 A * | 8/1996 | McKenna | ........... | A61B 1/0005 348/65 |
| 5,657,073 A * | 8/1997 | Henley | ................. | G03B 37/04 348/38 |
| 5,841,439 A * | 11/1998 | Pose | .................... | G06T 15/005 345/418 |
| 6,139,490 A * | 10/2000 | Breidenthal | ....... | A61B 1/00193 600/111 |
| 6,459,481 B1 * | 10/2002 | Schaack | ............... | A61B 5/1076 356/241.1 |
| 6,653,990 B1 * | 11/2003 | Lestruhaut | ............. | G06T 15/10 345/8 |
| 8,174,562 B2 | 5/2012 | Hartman | | |
| 8,928,746 B1 | 1/2015 | Stevrin | | |
| 9,077,973 B2 | 7/2015 | Aguren | | |
| 9,101,268 B2 | 8/2015 | Levy | | |
| 9,107,598 B2 | 8/2015 | Cheung | | |
| 9,124,802 B2 | 9/2015 | Steuart | | |
| 9,204,787 B2 | 12/2015 | Kazakevich | | |
| 9,277,122 B1 * | 3/2016 | Imura | ....................... | G06T 7/73 |
| 2001/0010546 A1 * | 8/2001 | Chen | .................. | H04N 5/23293 348/218.1 |
| 2002/0163499 A1 | 11/2002 | Sauer | | |
| 2004/0246333 A1 * | 12/2004 | Steuart, III | ........... | G03B 35/08 348/36 |
| 2006/0173242 A1 * | 8/2006 | Navok | .................... | A61B 1/07 600/133 |
| 2006/0293565 A1 * | 12/2006 | Uchimura | .......... | A61B 1/00121 600/156 |
| 2008/0007617 A1 * | 1/2008 | Ritchey | .................... | H04N 7/18 348/37 |
| 2013/0261633 A1 | 3/2013 | Thornberry | | |
| 2013/0296682 A1 | 11/2013 | Clavin | | |
| 2014/0135746 A1 | 5/2014 | Scheopp | | |
| 2014/0146132 A1 * | 5/2014 | Bagnato | ................. | G02B 30/34 348/36 |
| 2014/0275760 A1 | 9/2014 | Lee | | |
| 2015/0216403 A1 * | 8/2015 | Whitmore, III | ... | A61B 1/00114 600/103 |
| 2015/0272428 A1 * | 10/2015 | Nam | .................. | A61B 1/00181 600/109 |
| 2015/0348580 A1 * | 12/2015 | van Hoff | ............... | G06T 3/4038 348/38 |
| 2016/0119541 A1 * | 4/2016 | Alvarado-Moya | ........................ | H04N 5/2256 348/38 |
| 2016/0191887 A1 | 6/2016 | Casas | | |
| 2016/0225192 A1 * | 8/2016 | Jones | ..................... | A61B 34/10 |
| 2017/0013193 A1 * | 1/2017 | Cogal | .................. | H04N 5/2252 |
| 2017/0027650 A1 * | 2/2017 | Merck | ................ | A61B 1/00188 |
| 2017/0273549 A1 * | 9/2017 | Nazareth | ................. | G06F 3/017 |
| 2017/0296036 A1 * | 10/2017 | Newman | .............. | A61B 1/3132 |
| 2017/0322410 A1 * | 11/2017 | Watson | ................ | G02B 21/365 |
| 2018/0220100 A1 * | 8/2018 | Ovchinnikov | ........ | A61B 90/20 |

FOREIGN PATENT DOCUMENTS

WO    WO-2015133608 A1 *    9/2015    ............ A61B 90/37
WO    WO 2015/179446 A1    11/2015

* cited by examiner

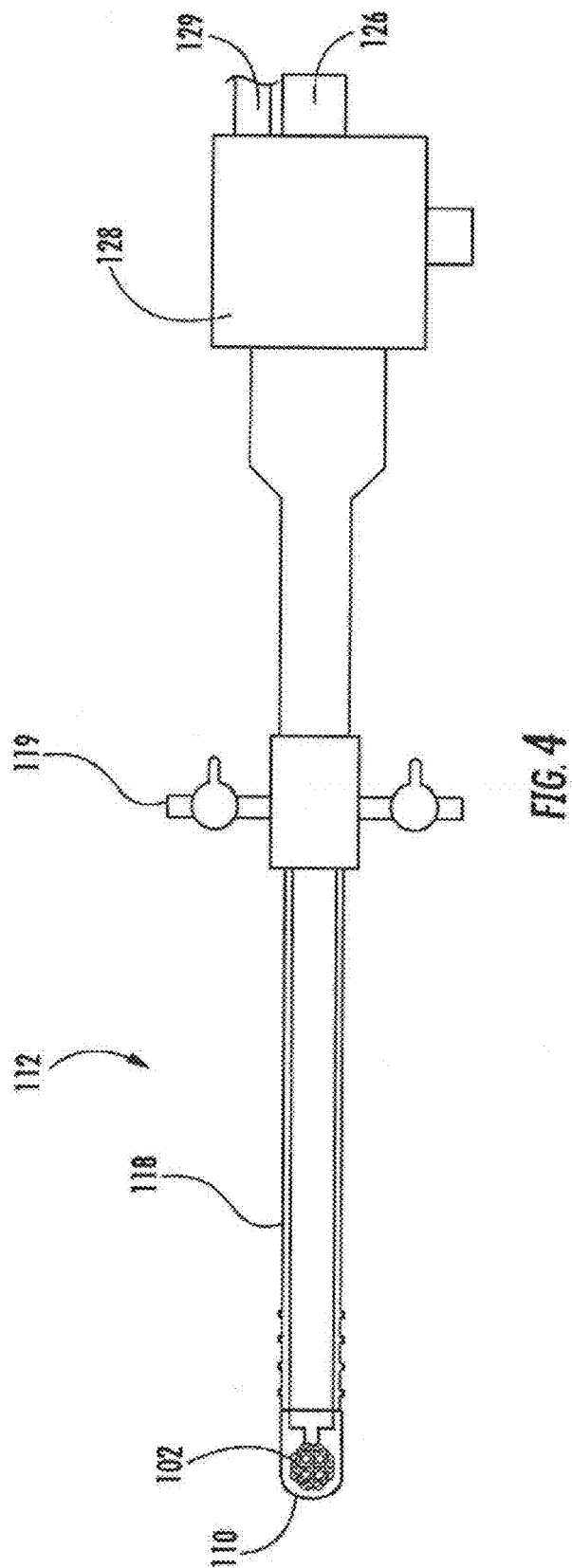

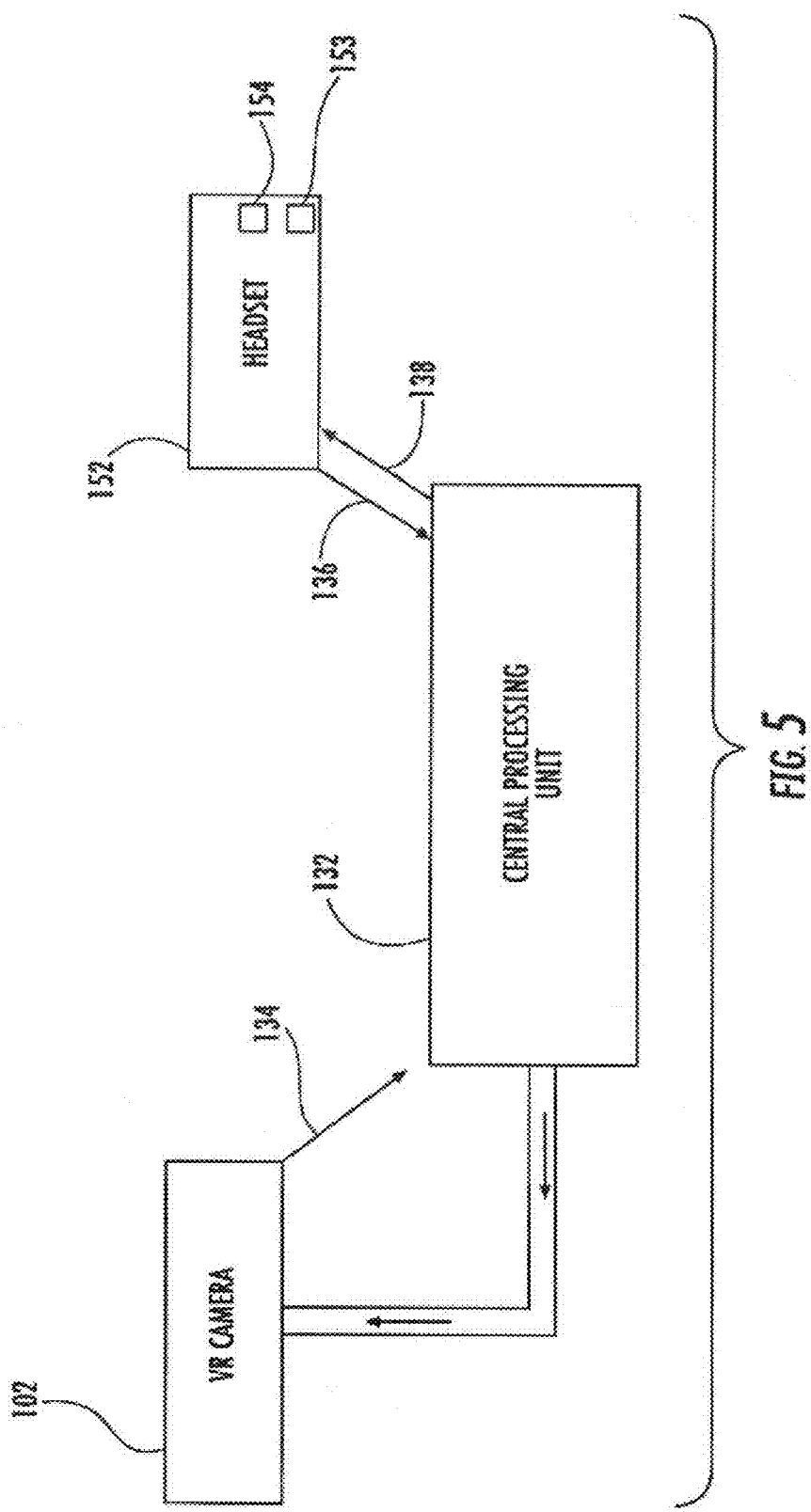

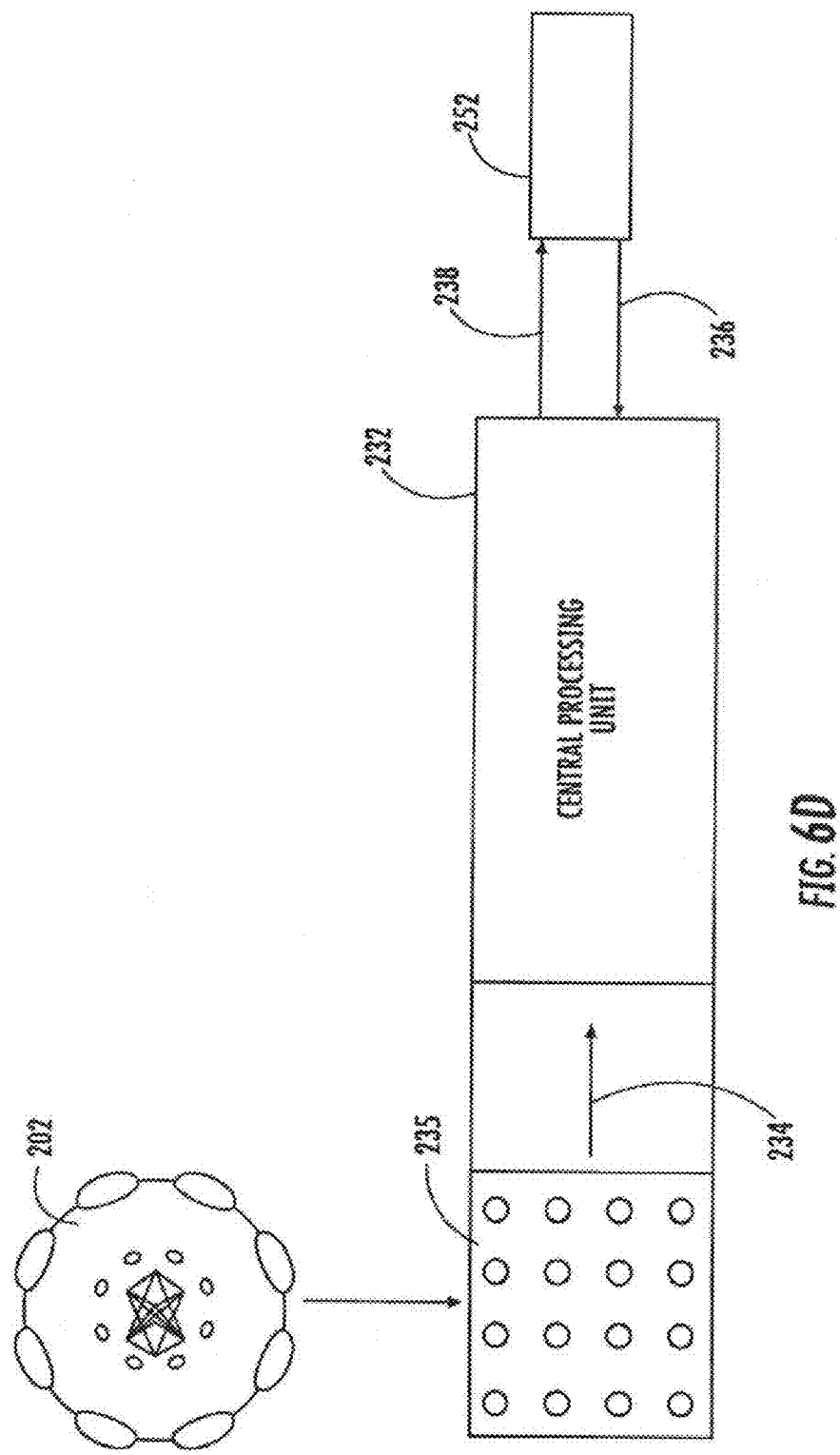

MIXED REALITY VIEWING OF A SURGICAL PROCEDURE

CROSS REFERENCES TO RELATED APPLICATIONS

This application claims priority on U.S. Provisional Application Ser. No. 62/509,273, filed on May 22, 2017, the disclosures of which are incorporated herein by reference.

BACKGROUND OF THE INVENTION

Field of the Invention

The subject technology relates generally to minimally invasive surgery and to virtual reality/mixed reality systems.

Description of Related Art

Minimally invasive surgery, such as with the use of laparoscopic instruments, allows for complex surgical procedures to be achieved without the comorbidities associated with open surgical techniques. Laparoscopic surgery allows for the diagnosis and treatment of numerous pathologies with only small incisions—wide enough to allow the passage of small laparoscopic instruments. However, laparoscopy comes at a cost to the surgeon's ability to operate with precision and ease, especially when visualization is limited by the laparoscopic instruments and viewing portals. During laparoscopy, the surgeon must insert laparoscopic instruments through small incisional portals in the patient's body cavity, such as the abdominal wall, intraluminal cavities, and intra-articular structures. The small portal sites constrains the location and motion of laparoscopic instruments and subsequently limits the surgeon's ability to view the internal body cavity and the surgical field.

Generally, new minimally invasive surgical procedures are most often optically guided, but such optical guidance methods do not permit full visualization and guidance of instruments or probes within (inside) the target tissue or organ. Incorporation of real-time, omnidirectional, 360-degree field of view stereoscopic visualization inside the body cavity would provide more accurate guidance.

The conventional techniques have been considered satisfactory for their intended purpose. However, there is an ever present need for improved visualization of the surgical field. This disclosure provides a solution for this problem via the utilization of virtual reality/mixed reality endoscopy.

SUMMARY OF THE INVENTION

A system for virtual reality and/or mixed reality viewing of a surgical procedure includes an endoscope having an elongated main body with a proximal end and an opposing distal end. A spherical element is coupled to the distal end of the endoscope. A plurality of cameras are aligned about the spherical element to allow 360 degrees of visualization, with each camera possessing a wide field of view. A fiber optic illumination strip is positioned around the periphery of the spherical element adjacent each camera. A central processing unit is in electronic communication with the plurality of cameras configured to receive real-time video feed from each of the plurality of cameras. A headset is electronically coupled to the central processing unit. The headset displays real-time video from a select portion of the plurality of cameras which provides a 360-degree stereoscopic view based upon the position of the headset.

A cable can be disposed through an internal channel of the endoscope configured to provide a source of power to the plurality of cameras and a source of light to the fiber optic illumination strip. A secondary processing unit can be housed at a proximal end of the endoscope electronically coupled to the central processing unit configured to process image input and output, and provide power to each of the plurality of cameras through the cable.

The central processing unit may include a processor operatively connected to a memory. The memory can include instructions recorded thereon that, when read by the processor, cause the processor to receive continuous real-time video feed from each of the plurality of cameras, receive spatial orientation data of the headset, compare the spatial orientation data of the headset with individual locations of each of the plurality of cameras, define a portion of the cameras that will provide a stereoscopic view that corresponds to the spatial orientation of the headset, and provide real-time video output from those cameras to the stereoscopic virtual reality or mixed reality headset.

The headset can include a headset processing unit including a processor operatively connected to a memory. The memory can include instructions recorded thereon that, when read by the processor, cause the processor to output spatial orientation data of the headset, receive real-time video output from the central processing unit, and display the real-time video output through a pair of digital lenses comprising the virtual reality or mixed reality headset.

A light source can be operatively coupled to the endoscope and cable configured to provide light to the fiber optic illumination strip. The endoscope can include an orientation marker at the proximal end configured to provide a physical representation of the orientation of the plurality of cameras. The plurality of cameras may be enclosed in clear, waterproof, autoclavable encasing attached to an outer tube of the endoscope.

The headset can further include a gyroscope configured to measure/determine a spatial orientation of the headset, particularly with respect to the surgical site. The gyroscope can be electronically coupled to the central processing unit. The virtual reality headset can be configured to partially obstruct a user's field of view thereby allowing the user simultaneous visualization of the real-time video feed as well as the surgical field. The virtual reality headset can also be electronically coupled to an actuation switch configured to toggle lenses of the headset from a position obstructing a user's vision to a non-obstructing position. Alternatively, a mixed reality headset can be configured to display the output of the endoscope, with visualization from the endoscope projected directly in front of the operator's field of view, leaving room in the operator's field of view for simultaneous visualization of the surgical field.

In another embodiment, a system for virtual reality/mixed reality viewing of a surgical procedure includes an endoscope having an elongated main body with a proximal end and an opposing distal end with a spherical element coupled to the distal end of the endoscope. Instead of cameras, a plurality of optical collection lenses are aligned about the spherical element. Each of the plurality of lenses have a corresponding objective lens positioned towards a center of the spherical element, similar to a microscope. A multi-focal plane apparatus is positioned at a central point of the spherical element. A fiber optic illumination strip is positioned around the periphery of the spherical element adjacent each camera. A secondary camera is positioned at a proximal end of the endoscope coupled to the multi-focal plane apparatus through an optic carrier tube. A central processing unit is in electronic communication with the camera configured to receive real-time video feed from each of the lenses. As previously described, a virtual reality or mixed reality headset is electronically coupled to the central processing unit. The headset may display real-time video from a select portion of the lenses. The plurality of lenses/cameras collectively may provide omnidirectional, 360 degree by 360 degree field of view capability, a portion of which may be displayed to the surgeon at a given time, based upon a position of the headset worn by the surgeon. The surgeon will thus be able to see the entire surgical site, by angling his/her head (i.e., up, down, left, and/or right), and may view the "surgical site" in all directions, including the portion of the site to be operated on, as well as portions laterally positioned thereto, and even back toward the surgical incision (i.e., a rearward view). This solves at least one major problem with current scopes in which the surgeon only sees the portion of the surgical site that is directly in front of the camera.

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

BRIEF DESCRIPTION OF THE DRAWINGS

So that those skilled in the art to which the subject invention relates will readily understand how to make and use the insertion instrument of the subject technology without undue experimentation, embodiments thereof will be described in detail herein below with reference to the following figures.

FIG. 4 is side view of the endoscope of FIG. 3 engaged with a sheath and trocar.

FIG. 5 is a schematic view of data flow using a system for virtual reality/mixed reality viewing of a surgical procedure having the virtual reality camera of FIG. 1 with a virtual reality headset or mixed reality headset

FIG. 6D is a schematic view of data flow using a system for virtual reality/mixed reality viewing of a surgical procedure having the virtual reality apparatus of FIG. 6A with a virtual reality headset.

DETAILED DESCRIPTION

Figure 1:
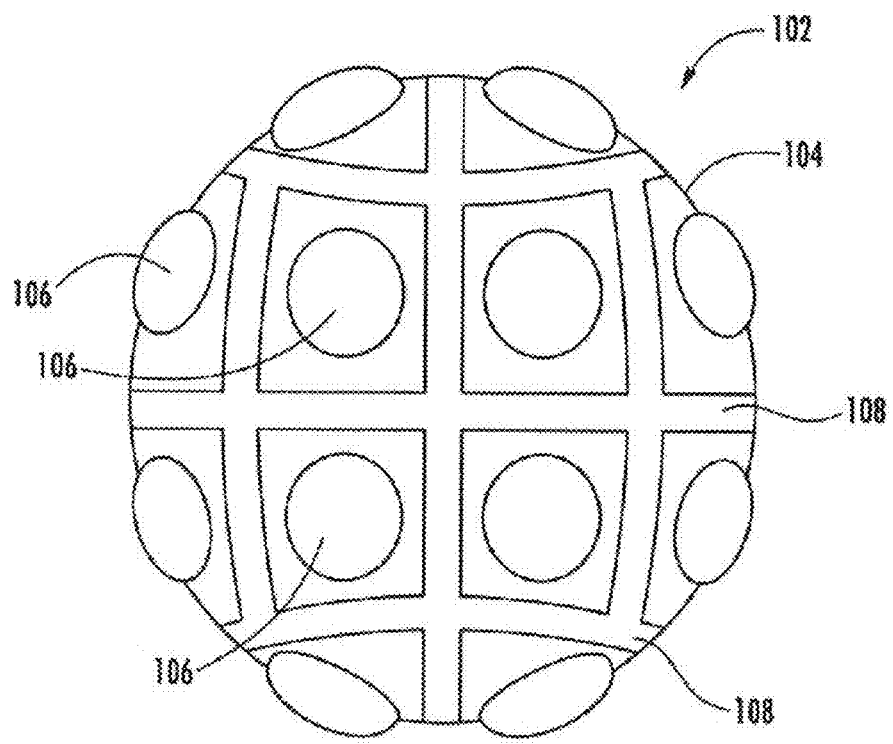
FIG. 1 is a top view of a virtual reality camera in accordance with a first exemplary embodiment of the subject technology, showing a plurality of cameras spherically aligned.

As used throughout this specification, the word "may" is used in a permissive sense (i.e., meaning having the potential to), rather than the mandatory sense (i.e., meaning must). Similarly, the words "include", "including", and "includes" mean including but not limited to.

The phrases "at least one", "one or more", and "and/or" are open-ended expressions that are both conjunctive and disjunctive in operation. For example, each of the expressions "at least one of A, B and C", "one or more of A, B, and C" and "A, B and/or C" mean all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference.

Furthermore, the described features, advantages, and characteristics of any particular embodiment disclosed herein, may be combined in any suitable manner with any of the other embodiments disclosed herein.

The present disclosure overcomes many of the prior art problems associated with real-time viewing of a body cavity and the like. The advantages and other features of the instruments and methods disclosed herein will become more readily apparent to those having ordinary skill in the art from the following detailed description of certain preferred embodiments taken in conjunction with the drawings which set forth representative embodiments of the present invention and wherein like reference numerals identify similar structural elements.

All relative descriptions herein such as left, right, up, and down are with reference to the Figures, and not meant in a limiting sense. The illustrated embodiments can be understood as providing exemplary features of varying detail of certain embodiments, and therefore, features, components, modules, elements, and/or aspects of the illustrations can be otherwise combined, interconnected, sequenced, separated, interchanged, positioned, and/or rearranged without materially departing from the disclosed systems or methods. The shapes and sizes of components are also exemplary and unless otherwise specified, can be altered without materially affecting or limiting the disclosed technology.

The present disclosure relates to a new type of surgical instrument, specifically an endoscope used for minimally invasive surgery. Referring to FIGS. 1-4 a portion of a system 100 for mixed reality viewing during a surgical or invasive medical procedure is shown. With reference to FIG. 1, a virtual reality (VR) camera assembly 102 with an omnidirectional, 360 degree field of view is shown. The VR camera assembly 102 may include a spherical element 104 with a plurality of individual cameras 106 strategically spaced around the element 104 to provide omnidirectional viewing. The number of cameras 106 and exact orientation of each camera 106 can vary. In one embodiment, the plurality of camera may be distributed about a portion of the spherical element 104. In another embodiment, the plurality of cameras 106 may be distributed about an entirety of the spherical element 104, and may be oriented in a pattern that will eliminate blind spots.

The following references utilize a camera: U.S. Pat. No. 3,473,872 to Okamura; U.S. Pat. No. 8,174,562 to Hartman; U.S. Pat. No. 8,928,746 to Stevrin; U.S. Pat. No. 9,077,973 to Aguren; U.S. Pat. No. 9,101,268 to Levy; U.S. Pat. No. 9,107,598 to Cheung; U.S. Pat. No. 9,124,802 to Steuart; U.S. Pat. No. 9,204,787 to Kazakevich; U.S. Patent App. Pub. No. 2016/0191887 to Casas; WO 01/05161 by Surgivision LTD; WO 2011/002209 by Univ. Ind.; and WO 2015/179446 by Samuel R. Brownd.

With the technology disclosed herein, each camera 106 may protrude slightly outwards from the surface of the spherical element 104. In one embodiment the cameras 106 may provide for wide angle viewing, and in another embodiment the cameras 106 may have a full 180 degree field of view or greater to capture real-time omnidirectional video. The cameras 106 are preferably digital cameras that provide high definition video, and may provide overlapping fields of view that through image processing may be merged to eliminate blind spots and produce a uniform display of the surgical site (see e.g., U.S. Pat. No. 5,657,073 to Henley, and U.S. Pat. No. 5,953,054 to Mercier). In yet another embodiment, each of the cameras 106 may be a fiber optic camera that may use a fiber optic cable, the size of which may be minimized, and which cables may be bundled together until reaching the VR camera assembly 102 where they may disperse and terminate on a respective portion of the spherical element 104.

During a surgical procedure the body cavity is completely dark making illumination within the surgical site essential. One or more fiber optic illumination strips 108 may be positioned around the periphery of the spherical element 104 adjacent each of the cameras 106. In one embodiment the fiber optic illumination strips 108 may each be formed the same as, or substantially similar to, the strip taught by U.S. Pat. No. 4,172,631 to Yevick. In another embodiment, rather than producing only an array of point light sources like the Yevick light strip, the fiber optic illumination strips 108 may instead each have a continuous slit that may permit a continuum of light to be emitted from the entire periphery/circumference of the illumination strip, which may encircle the entire spherical element 104. A plurality of fiber optic illumination strips 108 may form a grid-like network around the VR camera assembly 102, which may thus provide video feed from each camera 106 with ample lighting without taking away space from inside the spherical element 104. In one embodiment, only a single fiber optic illumination strip 108 may be used and may be positioned to encircle the spherical element 104 at any suitable orientation. In one embodiment it may be positioned at the equatorial plane 104E, and in another embodiment it may be positioned at a longitudinal plane. In another embodiment, two fiber optic illumination strips 108 may be used and may be positioned to encircle the spherical element 104 at both the equatorial plane and a longitudinal plane, which may be perpendicular to the equatorial plane. In other embodiments, fiber optic illumination strips 108 may be positioned at other longitudinal and/or latitudinal positions. Also, in certain embodiments the fiber optic illumination strips 108 may also fully encircle and/or partially encircle the spherical element 104. It should be noted that although the use of multiple fiber optic illumination strips 108 is described, a single integrally formed fiber optic illumination strip may be used for the emanation of light at the plurality of latitudinal and longitudinal positions.

Figure 2:
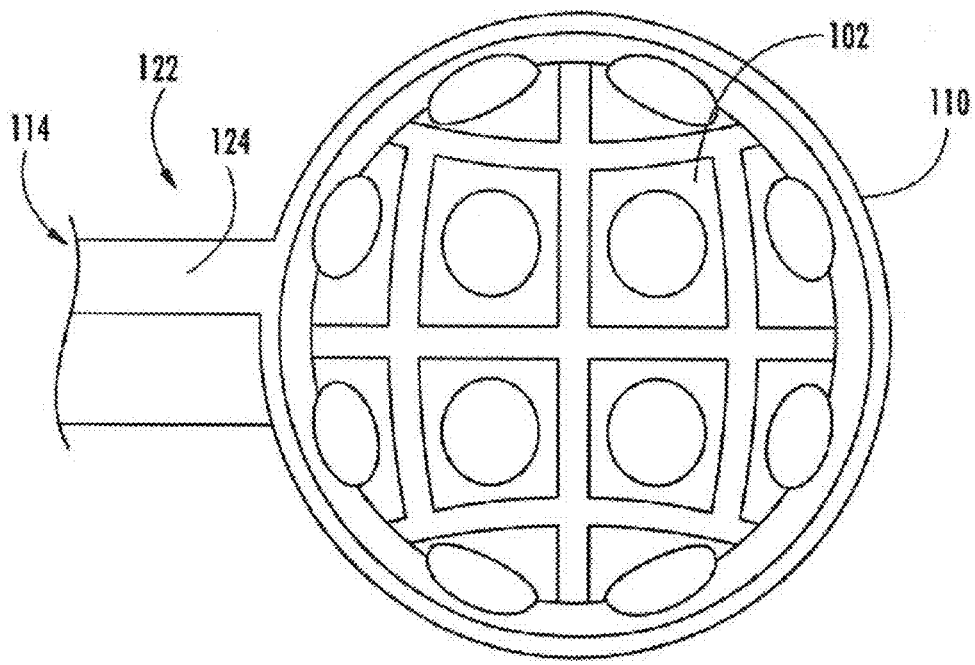
FIG. 2 is a side view of the virtual reality camera of FIG. 1, showing an outer waterproof casing.
Figure 3:
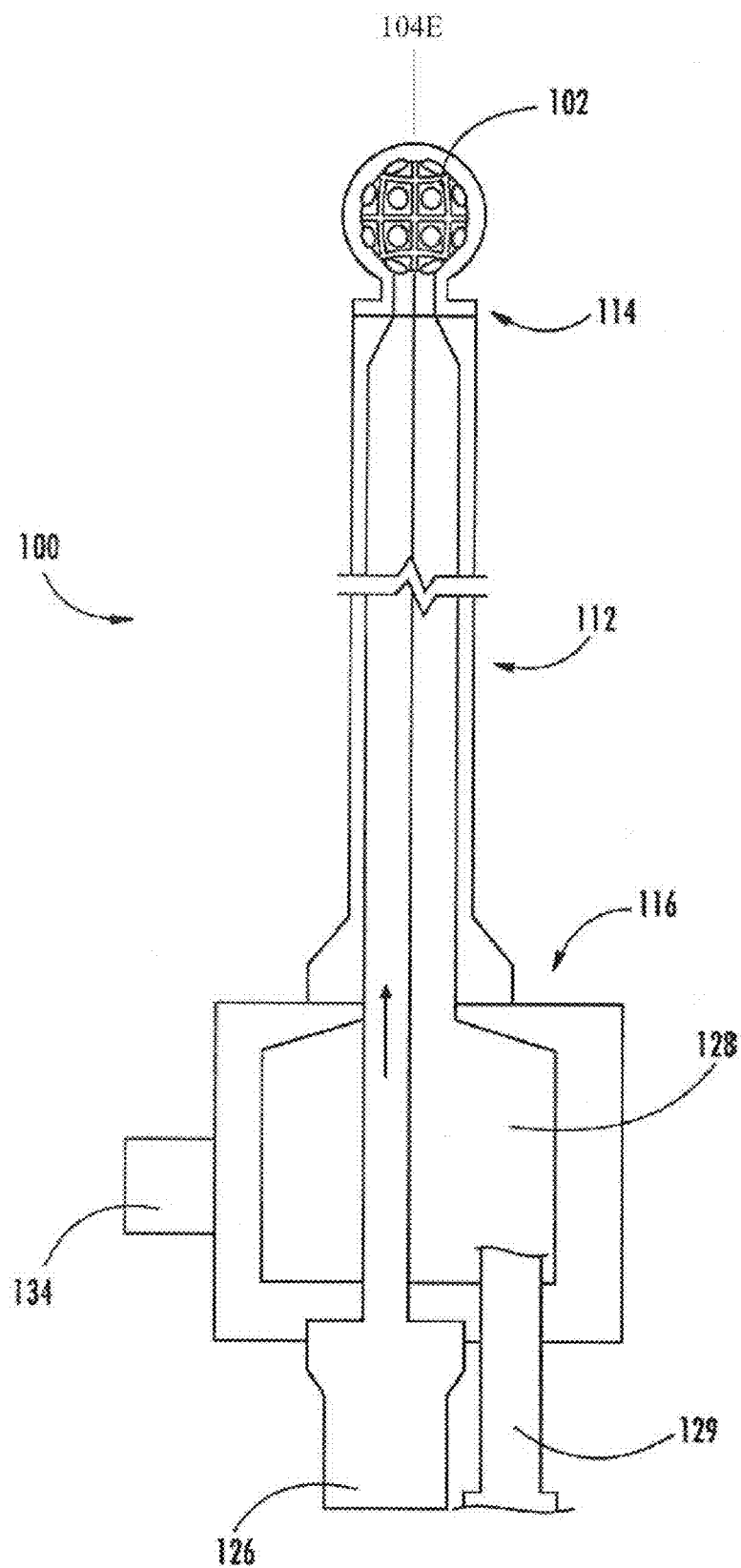
FIG. 3 is a side view of an endoscope having the virtual reality camera of FIG. 1 on a distal end thereof.

With reference to FIGS. 2 and 3, the spherical element 104 may be coupled to a distal end 114 of an endoscope 112 by a strut 122 that may house a cable 124. The cable 124 may provide power to the cameras 106 and light to the fiber optic illumination strip 108. The cable 124 may connect directly to an external light source 126 and a secondary processing unit 128 both of which may be positioned at a proximal end 116 of the endoscope 112. The cable 124 may also house the fiber optic bundle when utilized. Also shown in FIG. 2, the VR camera assembly 102 may be enveloped by a clear, waterproof, autoclavable encasing 110, which may be used if the VR camera assembly 102 cannot be made waterproof.

Referring now to FIG. 3, the VR camera assembly 102 may receive power from the secondary processing unit 128, which may be directly connected to a central processing unit 132 (shown in FIG. 4). The secondary processing unit 132 may collect visual input from the VR camera assembly 102, and organize and relay the data to a central processing unit 132. An orientation marker 134 may be provided near the proximal end 114 of the endoscope 112 to provide the surgeon with a physical representation that calibrates to an "up" position of the VR camera assembly 102. Also near the proximal end 114 may be a power cable 129 to provide power to the secondary processing unit 106 and VR camera assembly 102.

The endoscope 112 can engage with a commercially available instrument sheath 118 and trocar 119 known in the art, best seen in FIG. 4. The sheath 118 may be used to provide saline inflow and outflow to the distal end 114 of the endoscope 112.

Referring now to FIG. 5, a schematic view of the data flow within the system is shown, including the VR camera assembly 102, the central processing unit 132 and a headset 152. The synchronized video feed 134 from the cameras 106 is sent through the camera cable 124 to the secondary processing unit 128, and ultimately to the central processing unit 132. The central processing unit 132 may also record each of the camera's 106 positions. By having the central processing unit 132, light source 126, and power cable 129 of the VR camera assembly 102 external to the camera assembly 102, the space inside the spherical element 104 can be reserved for maximizing optical video fidelity.

The central processing unit 132 may be in electronic communication with the headset 152. More specifically, the central processing unit 132 may communicate with a headset processing unit 154 (shown schematically). The headset 152 can be worn by a surgeon during an operation for the surgeon see any portion of the entire stereoscopic 360 degree by 360 degree field of view of the internal body cavity of the patient, and a simultaneously view the real-life surgical field, as will be discussed in further detail.

The headset 152 may include a gyroscope 153 (shown schematically) which may permit determining/setting of a baseline spatial orientation with respect to the surgical site (e.g., a line of site of the incision, or a line of site directly at a center of a target organ), and may provide spatial orientation data/changes 136 (i.e. direction, rotation, tilt, etc.) of the headset 152 with respect to the baseline orientation. The spatial orientation 136 of the headset 152 is sent to the central processing unit 132 through the headset processing unit 154. The central processing unit 132 processes the spatial orientation 136 of the headset 152, and changes thereto, and outputs only the appropriate video feeds 138 from the VR camera assembly 102 to the headset 152. In other words, the headset processing unit 154 only receives stereoscopic video feeds 138 from the VR camera assembly 102 that correspond to the spatial orientation 136 of the headset 152. While all of the cameras 106 will be active continuously, the video feeds 134 displayed to the operator through lenses of the headset 152 will be determined primarily by the position, tilt, and rotation of the headset 152.

For example, if the headset 152 is pointing up and tilted to the right, the central processing unit 132 will compare this spatial orientation with the position of each of the cameras 106 and determine a portion of the cameras that display a real-time corresponding stereoscopic view. In this example, the central processing unit 132 will output a video feed 138 from the upper cameras 106 on the right side (based on the orientation marker 134) of the VR camera assembly 102 to the headset processing unit 154. If the headset 152 is pointed to the right and subsequently rotates to the left, the central processing unit 132 will output a video teed 138 first from the right cameras, next from the middle cameras, and then from the left cameras, which video will be displayed through the headset 152 sequentially. Essentially, the system 100 provides real-time, omnidirectional, stereoscopic, virtual reality viewing capability of the internal surgical field, and based on positioning of the headset 152, the surgeon may view any portion of the internal operational site.

In one embodiment, the gyroscope and processor may be configured such that moving of the surgeons head beyond a threshold amount (e.g., greater than 5 degrees laterally or 5 degrees upwardly or 5 degrees downwardly) may cause the video supplied to the headset to continuously scroll in that direction at a desirable rate (e.g., 5-10 degrees per second), until the surgeon moves his/head back to be below the threshold amount. This may enable the surgeon to quickly see a view of the internal body cavity that may be 180 degrees away from the current view, in a short amount of time. In one embodiment, the more the surgeon moves his/her head beyond the threshold amount, the faster may be the scrolling through the 360 degree by 360 degree omnidirectional video for display in the headset.

With reference to FIGS. 6A-6D, another embodiment of a system 200 for virtual reality viewing of a surgical field is shown using an omnidirectional multi-axis lens apparatus 202. The external appearance of the apparatus 202 looks identical to the spherical housing 104 of VR camera assembly 102. Similar to cameras 106, collection lenses 206 of the multi-axis lens apparatus 202 are arranged spaced around a spherical element 204 to collect omnidirectional 360 degree light. A fiber optic illumination strip (not shown for purposes of clarity), similar to fiber optic illumination strip 106, may be positioned adjacent each of the collection lenses 206 to provide lit images within the body cavity.

The omnidirectional multi-axis lens apparatus 202 may function similar to a microscope in that it collects light from a plurality of collection lenses 206 on the external surface of the sphere 204 and sends the light through an optic carrier tube 266 into a camera 272 located at the proximal end of the endoscope.

Figure 6A:
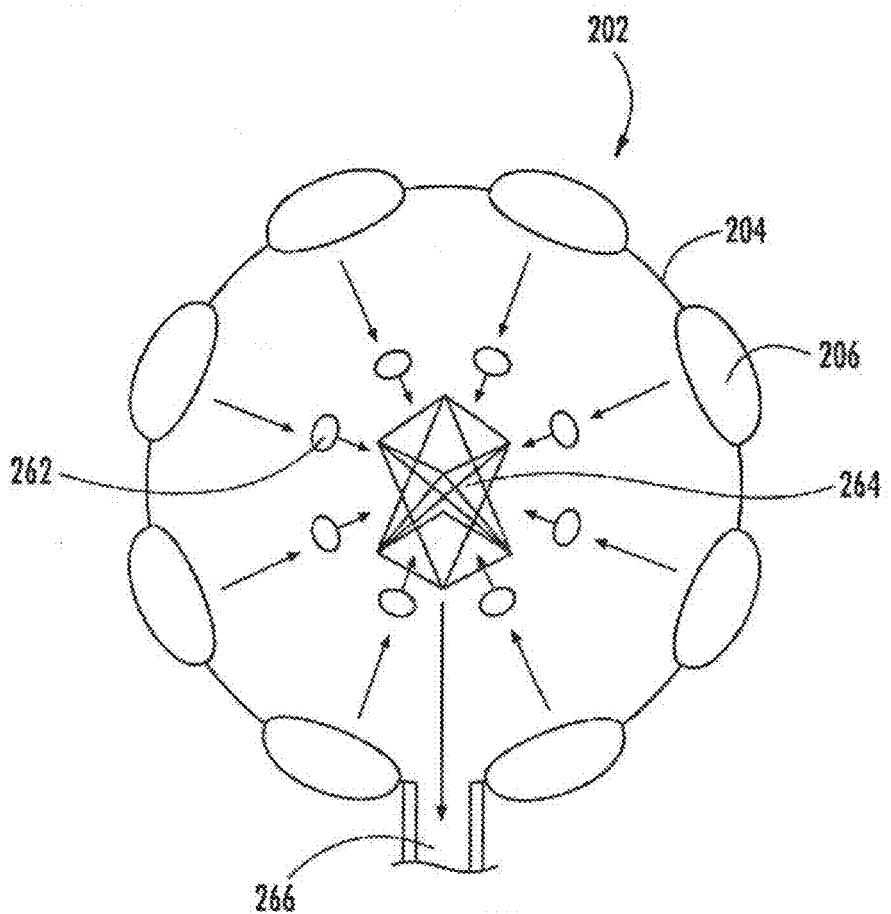
FIG. 6A is a top view of another exemplary embodiment of a virtual reality apparatus.
Figure 6B:
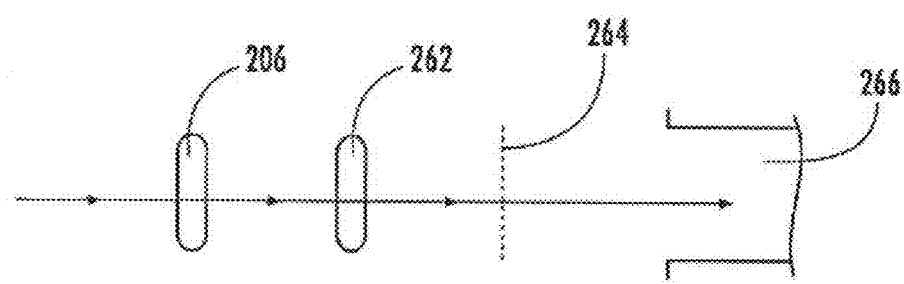
FIG. 6B is a schematic view of an image as sent through one collection arm of the virtual reality apparatus of FIG. 6A

A multi-focal plane apparatus 264 may be positioned at a center point of the multiple lens apparatus 202 that is designed to collect light from each collection lens 206, and may send all inputs through to an optic carrier tube 266. A schematic representation of the image as sent through one collection arm of the collection lens 206, objective lens 262 a focal plane 264 to the optic carrier tube 266 is best shown in FIG. 6B.

Instead of one image being sent to the user's eye like a microscope, there may be multiple images 235 being sent to a camera 272. The camera 272 converts the images to multiple video feeds 234 that may be sent to central processing unit 232. The central processing unit 232 may filter and process the images, and sends the appropriate stereoscopic video feed 238 to the headset 252 depending on the orientation of the headset, similar to central processing unit 132.

Figure 6C:
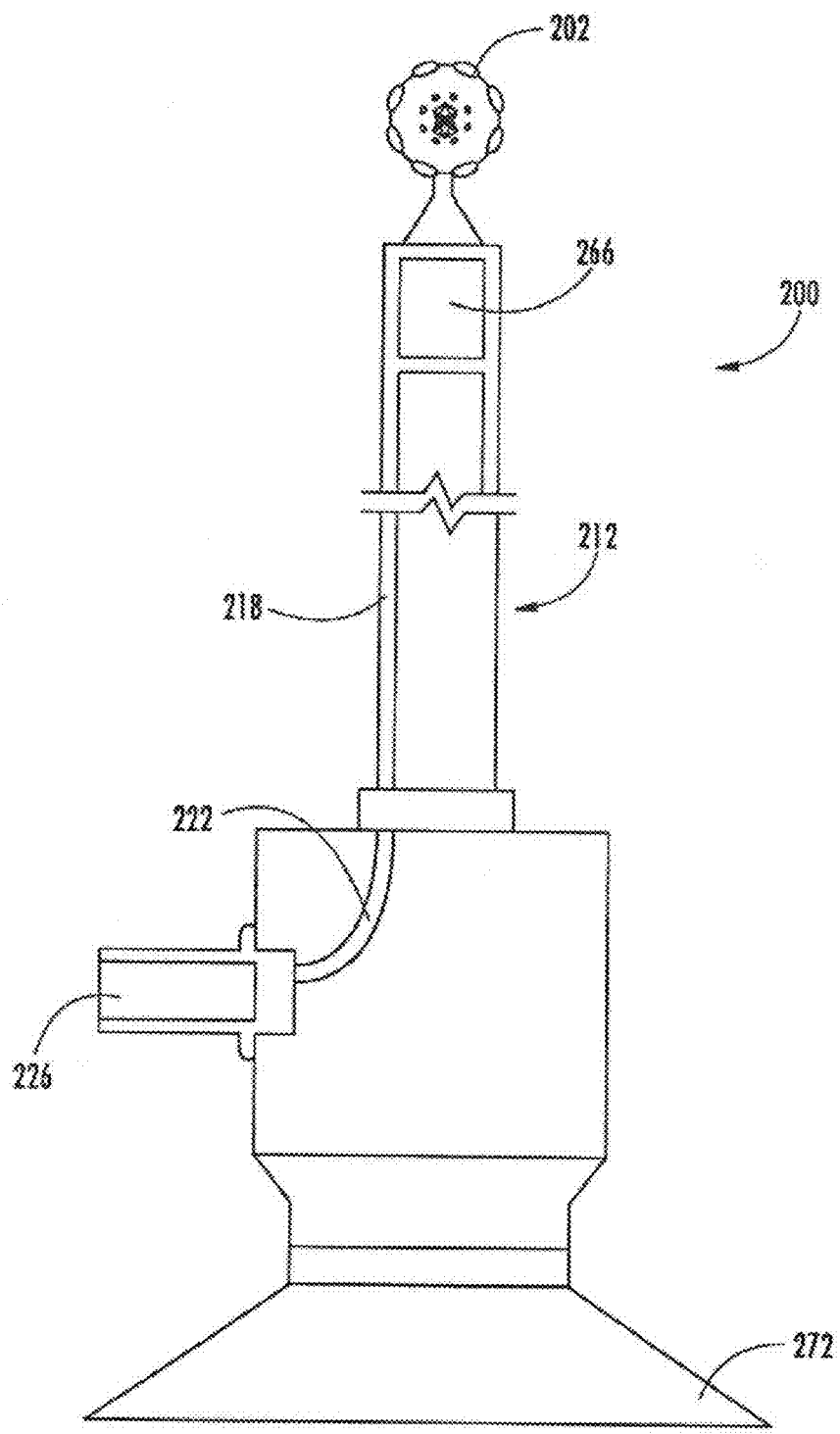
FIG. 6C is a side view of an arthroscope having the virtual reality apparatus of FIG. 6A on a distal end thereof.

As in the previous embodiment, the omnidirectional multi-axis lens apparatus 202 can be coupled with a surgical instrument for minimally invasive surgery. FIG. 6C shows the omnidirectional multi-axis lens apparatus 202 attached to the distal end of an arthroscope 212. The arthroscopic 212 assembly proximal to the apparatus 202 may be similar or identical to commercially available arthroscopes and endoscopes. As in the previous embodiment, an external light source 226 may provide power to fiber optic illumination strips through a cable 222.

FIG. 6D illustrates the data flow of system 200 using the omnidirectional multi-axis lens apparatus 202 with the central processing unit 232 and headset 252. The central processing unit 232 receives spatial orientation output 236 from the headset processing unit 154. Depending on the spatial orientation of the headset 252 (rotation, tilt, rotational velocity, etc.), the central processing unit 232 will output real-time selective video feed 238 to the headset 252 that corresponds to its spatial orientation. Thus, if the user rotates his/her head to the right, the video feed 238 will display stereoscopic video from the right side of the lens apparatus 202, similar to the mechanism described in FIG. 5.

A prior art headset that entirely covers both eyes (i.e., the entire field of view of the user's eye is taken up by the headset), such the user only sees what is displayed through the headset is unacceptable in a surgical situation, since the surgeon needs to be able to see his/her own hands and the surgical field.

Figure 7A:
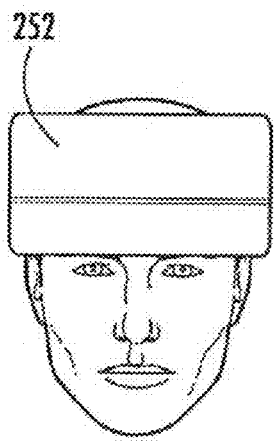
FIG. 7A is a front view of a first exemplary embodiment of a partial field-of-view virtual reality headset of the subject technology.
Figure 7B:
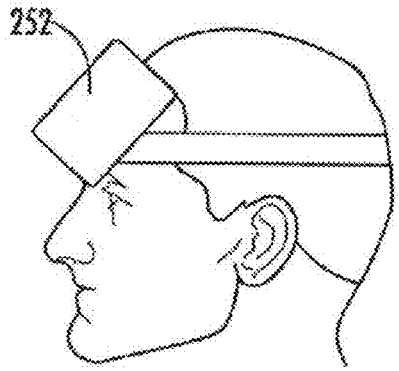
FIG. 7B is a side view of the partial field-of-view virtual reality headset shown in FIG. 7A.
Figure 7C:
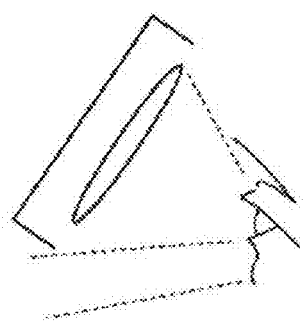
FIG. 7C is a side cross-sectional view through the partial field-of-view virtual reality headset shown in FIG. 7A.

A detailed view of an exemplary embodiment of the headset 252 is shown in FIGS. 7A-7C. The headset 252 is a partial field-of-view virtual reality headset which allows the field of view from the VR camera assembly 102 or multi lens apparatus 202 to be displayed directly over the user's field of view while seamlessly and simultaneously allows visualization of the surgical field. To accomplish this headset 252 only obstructs a portion of the field of view of the surgeon. The headset 252 may be angled in the cephalad direction and does not entirely cover the eyes. If the user looks upwards, the user will see the video feed output from the central processing unit 132 or 232 (see FIG. 7C). If the user looks downwards, the user will see the real-life field of view. Approximately 50-70% of the surgeons field of view may be taken up by the headset 252, while the remaining field of view (visualized by looking downwards) may allow the surgeon to see his/her own hands and the real-life surgical site. This simultaneous visualization of the stereoscopic video feed as well as the actual surgical field, as illustrated in FIGS. 7F-7G, will allow a surgeon to perform arthroscopic/endoscopic surgery more effectively/efficiently. In other embodiments, various different shapes for the headset and positioning of the image therein may be used (see e.g., headset 252A in FIG. 7F).

Figure 7E:
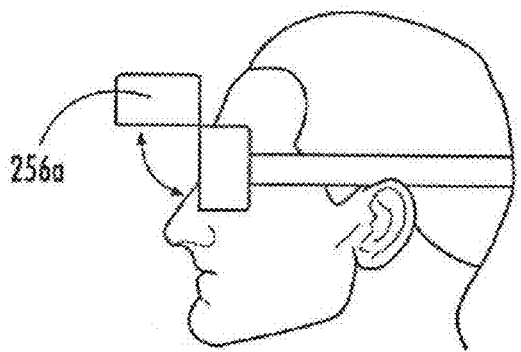
FIG. 7E is the side view of FIG. 7D, shown with the portion of the head set after being moved into a second position that provides the surgeon's eyes with a direct and unobstructed view of the operating site.
Figure 7D:
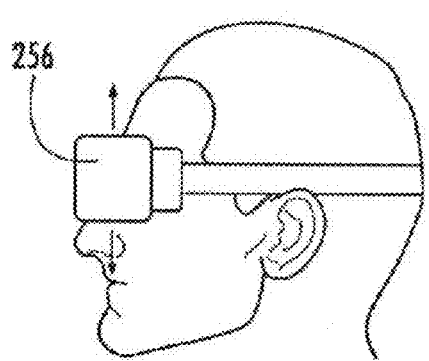
FIG. 7D is a side view of another exemplary embodiment of a partial field-of-view virtual reality headset of the subject technology, shown with a portion of the headset in a first position that allows the surgeon to see the video feed in the headset.
Figure 7F:
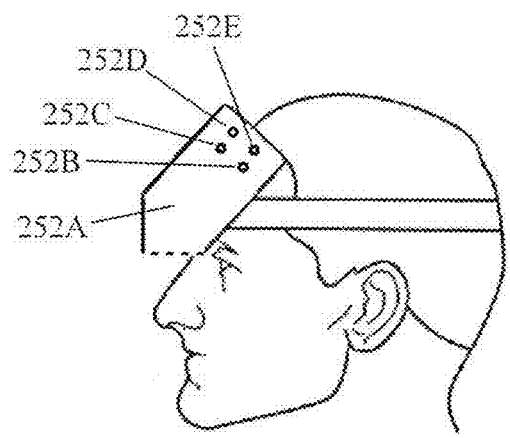
FIG. 7F is a front view of another embodiment of a partial field-of-view virtual reality headset of the subject technology.
Figure 7G:
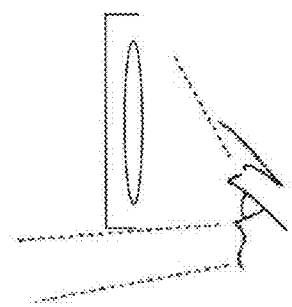
FIG. 7G is a side cross-sectional view through the partial field-of-view virtual reality headset shown in FIG. 7F.

Another embodiment of the headset 256 is shown in FIGS. 7D-7E. In this embodiment, lenses 256a of the headset 256 hinge or slide open allowing a surgeon to view the real-life surgical field when the lenses are a distance away from the surgeon's eyes. An actuation switch (not shown) such as a button on the endoscope or a foot pedal toggles (e.g., pivots) a portion of the headset 256 between a first position allowing the surgeon to see the video feed in the headset, and a second position that removes the lenses from the surgeon's eyes, allowing the surgeon's eyes a clear, unobstructed field of view of the operating site.

In yet another embodiment, an existing apparatus for providing the video feed may be used, such as the Google Glass, as shown for example by U.S. Pat. No. 9,285,592. A variation of that apparatus may alternatively be used, which variation may appropriately reposition the viewing display screen of the device to the upper portion of the wearer's field of view (see FIG. 7J), and may also provide a second such screen for viewing of the two screens respectively by the wearer's two eyes.

Figure 8:
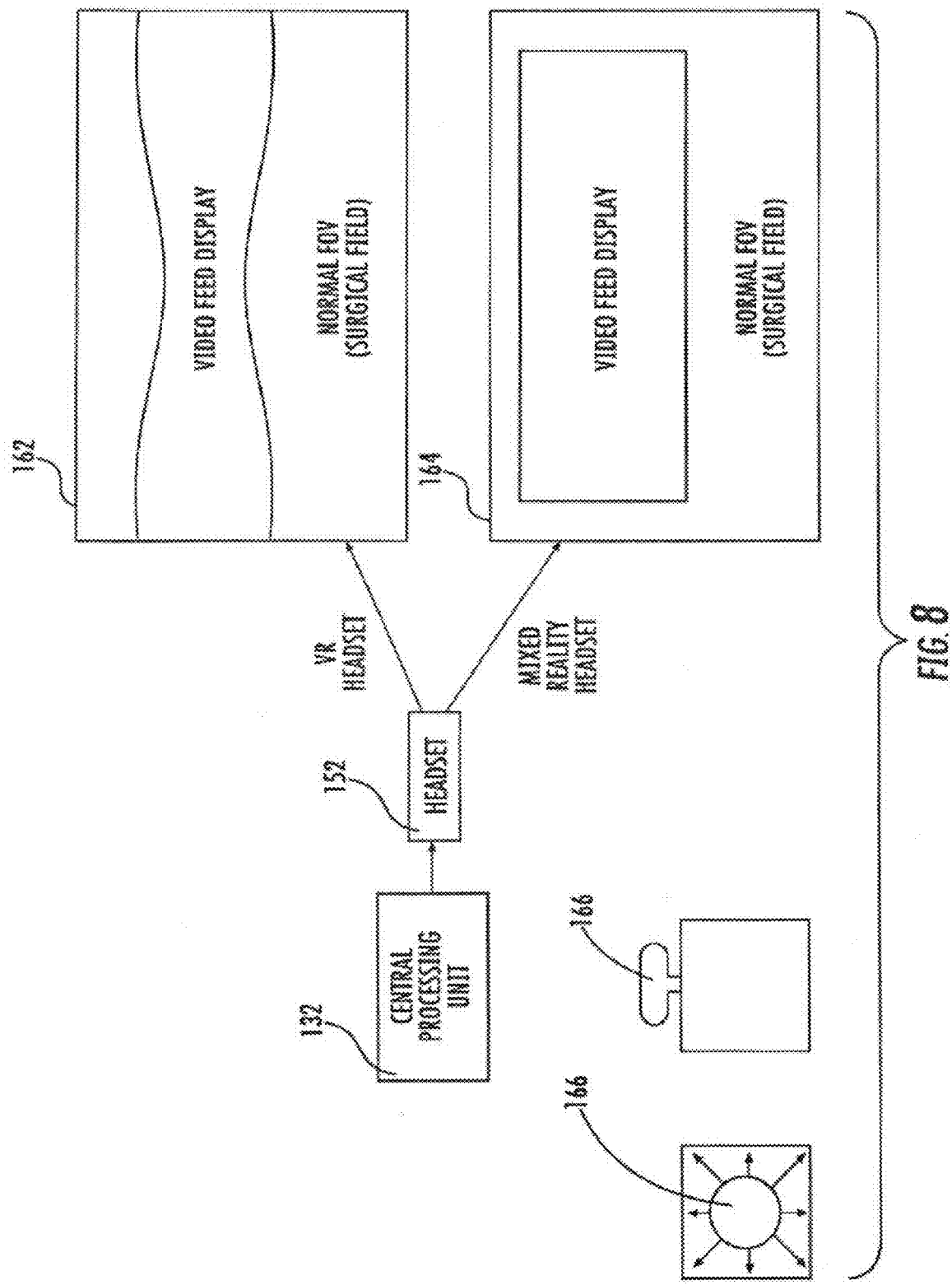
FIG. 8 is a schematic diagram showing the fields of view of a surgeon wearing a virtual reality headset or mixed reality headset.

FIG. 8 schematically illustrates the surgeon's field of view (shown in boxed 162 and 164) when wearing either a VR headset or a mixed reality headset during surgical procedures. In both scenarios, the central processing unit 132 may send the appropriate stereoscopic video feed to the headset 152. If the user is wearing a VR headset with partial field of view (as described in FIG. 7B), he or she will see the image in box 162. The video feed will be visualized by looking upwards. By looking downwards, the normal field of view (the surgical field) will be visualized.

If the user is wearing a mixed reality headset, the video feed will be projected directly into the user's field of view as pictured, as shown in box 164. Again, by looking upwards, the surgeon sees the video feed from the VR camera assembly 102 or multi-axis lens apparatus 202. By looking downwards, the surgeon is able to look at his/her own hands and the real-life surgical field. The size and location of the video feed display may be completely customizable depending on the user.

In both images, the central processing unit video feed may take up 45-70% of the FOV. In other embodiments this percentage for the field of view can be changed depending on the surgeon's preference, by using a button on the headset (e.g., button 252B for headset 252A in FIG. 7F). For example, some surgeons will prefer the video feed to be smaller and take up less of the field of view, if the majority of the surgery is dependent on real-life surgical manipulation and instrumentation. Other surgeons will prefer the video feed to be larger and take up more of the field of view, if the majority of the surgery requires detailed visualization from the endoscope apparatus. Other system parameters may also be modified for the video feed provided to the surgeon, For example, button 252C may be used to adjust the sensitivity of the video feed movements provided based on the motion of the surgeon's head, to make the movement of the video feed provided (e.g., moving right to left or left to right) more or less responsive to movement of the surgeon's head in moving right to left or left to right. Button 252D may be used to zoom in or out on the surgical site, where such zoom capability is provided by the cameras used. Button 252E may be an on/of switch. Alternatively, buttons 252A-E can be implemented as a part of the proximal endoscopic apparatus so that adjustments can be made in the sterile field. Another alternative is to implement these buttons as switches near the surgeon's foot.

Figure 7H:
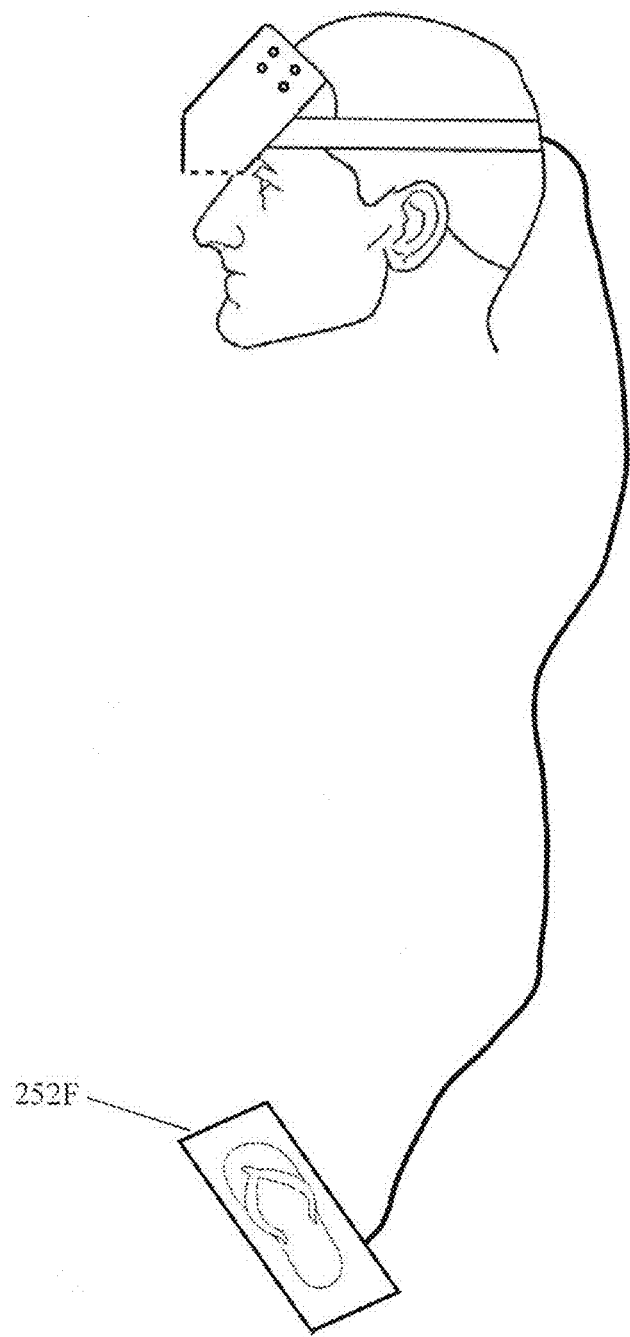
FIG. 7H illustrates the partial field-of-view virtual reality headset of FIG. 7F, shown coupled to a pressure pad configured to scroll the image displayed in the headset according to shifting of the weight of the surgeon foot on the pad.
Figure 7I:
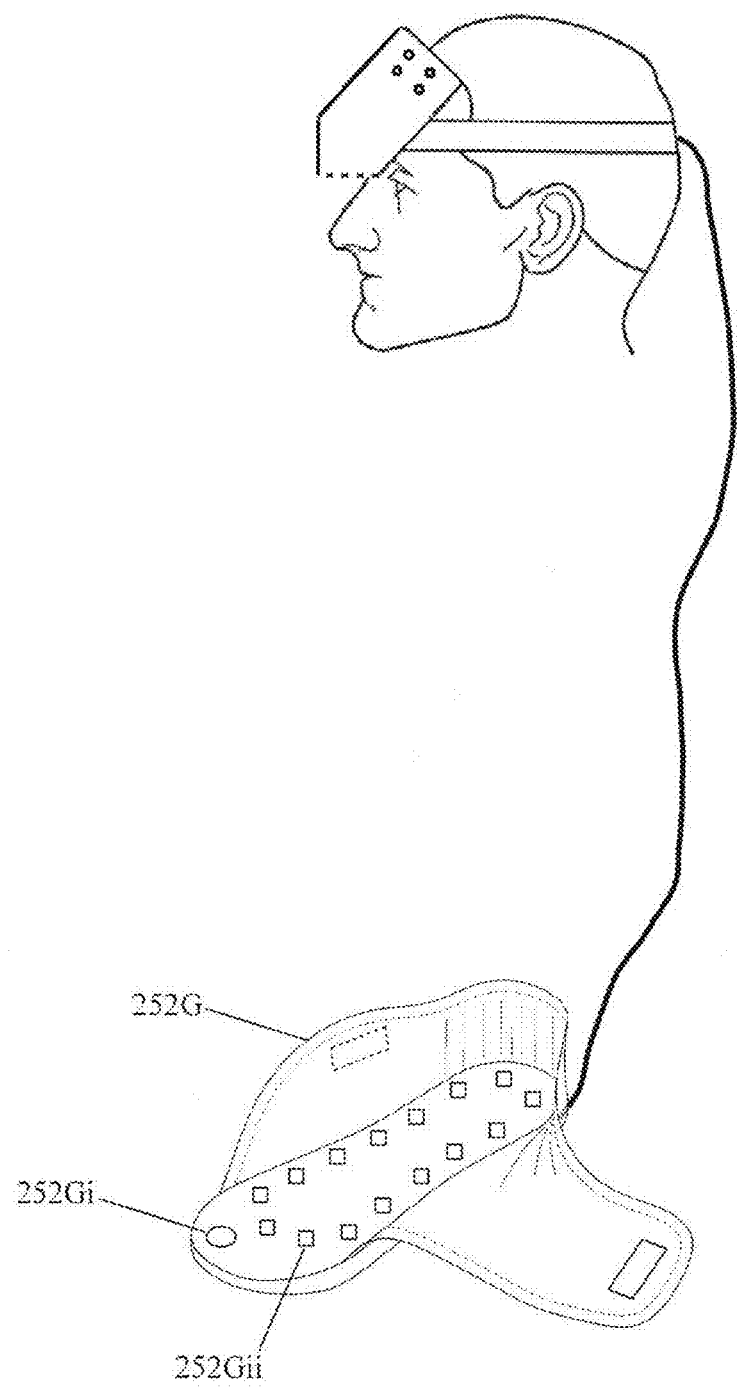
FIG. 7I illustrates the partial held-of-view virtual reality headset of FIG. 7F, shown coupled to a foot orthotic with built-in pressure sensors configured to sense weight changes of the wearer to scroll the image displayed in the headset according to shifting of the weight of the surgeon's foot within the orthotic.
Figure 7J:
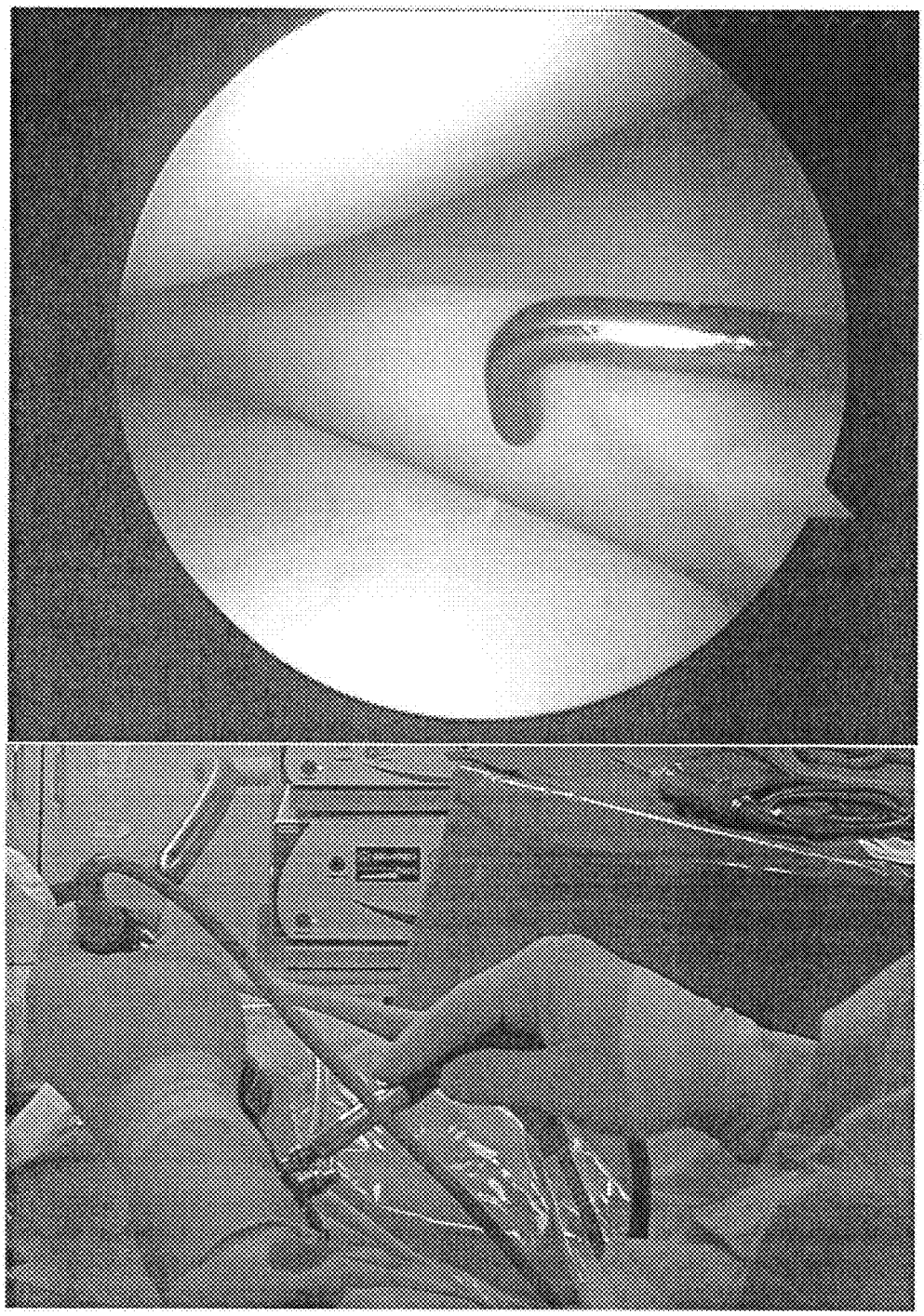
FIG. 7J illustrates the dual visualization capability provided to the surgeon by the subject technology, in the form of the video feed in the upper portion of the figure, as seen through the headset, and the actual surgical field in the bottom portion of the figure.

In another embodiment, the partial field-of-view virtual reality headset of FIG. 7F may be coupled to a foot pedal that may be used to cause scrolling of the video feed provided to the surgeon, such that when the surgeon moves his/her foot to the left or to the right, the image correspondingly scrolls left or right, and when the surgeon moves his/her foot up/forward or down/backward, the image correspondingly scrolls up or down, In yet another embodiment, shown in FIG. 7H, the partial field-of-view virtual reality headset of FIG. 7F may be coupled to a pressure pad 252F. The pressure pad 252F may be configured to scroll the image displayed in the headset according to shifting of the weight of the surgeon's foot upon the pad, which may provide stable support for the surgeon's foot. Any suitable pressure pad may be used, including, but not limited to, the pad shown by U.S. Pat. No. 6,788,295 to Inkster. In yet another embodiment, shown in FIG. 7H, the partial field-of-view virtual reality headset of FIG. 7F may be coupled to a foot orthotic 252E that may have a plurality of pressure sensors 252Gii, which foot orthotic may instead be worn by the surgeon. The plurality of pressure sensors 252Gii of the foot orthotic 252G may detect the pressure distribution applied by the surgeon's foot, from the ball to the heel, and from the inside to the outside, to correspondingly control scrolling of the image displayed in the headset up, down, left, and right. The surgeon may prevent scrolling of the displayed image merely by keeping his/her foot evenly balanced, or alternatively, a switch 252Gii may be toggled by the surgeon's toe to quickly/easily activate and deactivate the scrolling caused by the sensors, when desired by the surgeon.

FIG. 8 further shows schematically a diagram of an analog control knob 166 that can be located at the proximal end of the endoscope, for example endoscope 112. The control knob 166 allows change in direction of the field of view. For example, by pushing the knob 166 to the left, the video feed will pan left, allowing the surgeon to visualize leftwards without moving his/her head. Therefore, the control knob 166 allows for another way to visualize and control the video feed without tilting or moving the headset 152.

As will be appreciated by one skilled in the art, aspects of the present embodiments may be embodied as a system, method or computer program product. Accordingly, aspects of the present embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized, any of which may be a non-transitory computer readable storage medium. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable. RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 9:
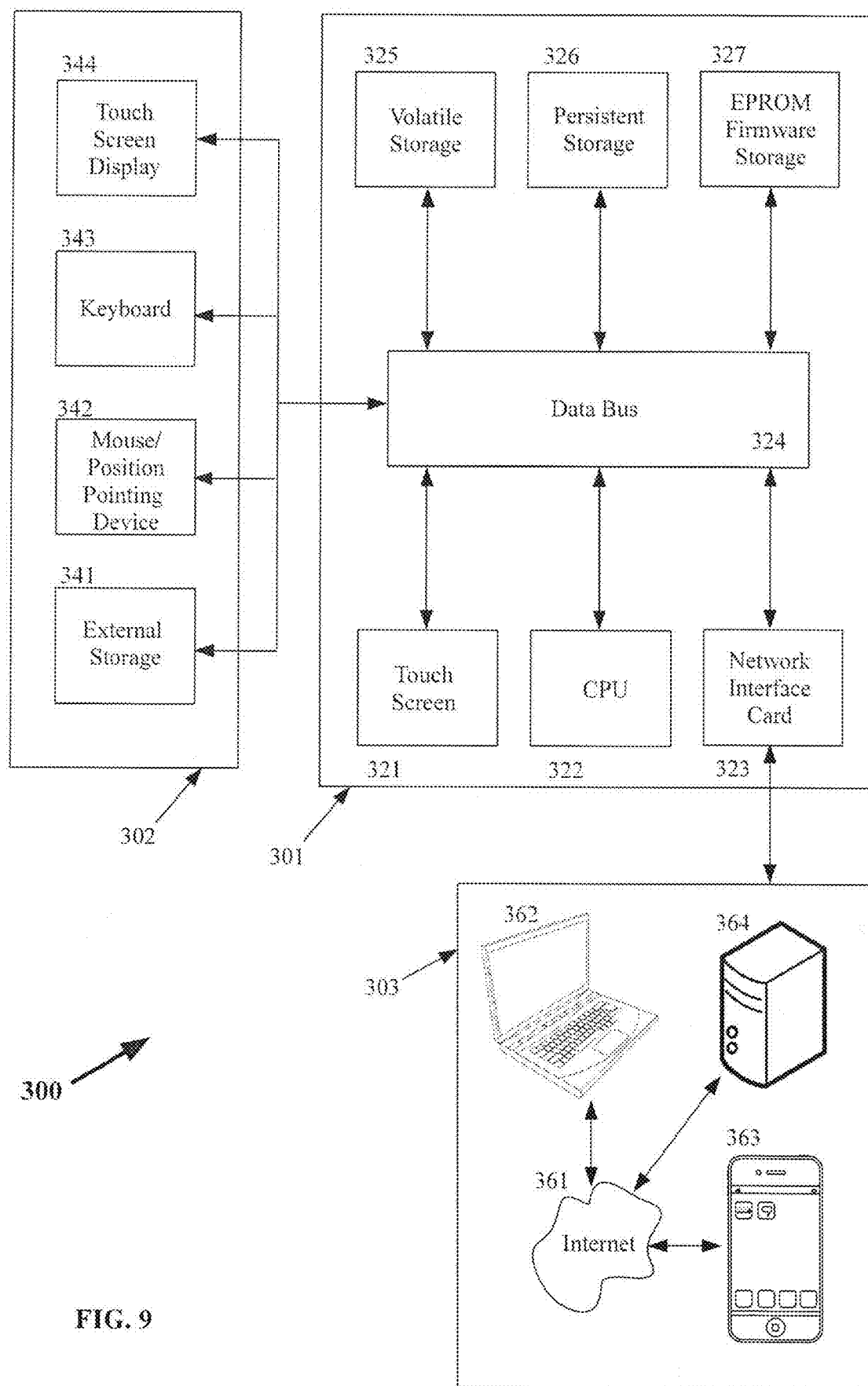
FIG. 9 is a schematic illustration showing an exemplary computing unit capable of being programmed by the instructions of software programming code for the present invention, and which may include personal computers, cellular phones, and other mobile computing devices.

An exemplary computer system 300 is shown schematically in FIG. 9 and may include computing unit 301 interacting with external peripherals 302, such as a separate touch screen display 344, and interacting with network resources 303, including use of the internet 361, and other computers (or other client devices or a server), which may be a laptop computer 362 (i.e., a second client device associated with a second user), a smart phone 363 (i.e., a third client device associated with a third user), a server 364, etc.

The computing unit 301 may include a data bus 324 for communicating information across and among various parts of computing unit 301, and a central processing unit, which may be a microprocessor (hereinafter "processor" or "CPU") 322 coupled with a bus 324 for processing information and performing other computational and control tasks. Computing unit 301 may also include a volatile storage 325, such as a random access memory (RAM) or other dynamic storage device, coupled to bus 324 for storing various information as well as instructions to be executed by processor 322. The volatile storage 325 may also be used for storing temporary variables or other intermediate information during execution of instructions by processor 322. Computing unit 301 may further include a read only memory (ROM) or an erasable programmable memory (EPROM) 327 or other static non-transitory storage device coupled to bus 324 for storing static information and instructions for processor 322, such as basic input-output system (BIOS), as well as various system configuration parameters. A persistent storage device or non-volatile memory 326, such as a magnetic disk, optical disk, or solid-state flash memory device may be provided and may be coupled to bus 324 for storing information and instructions.

Computing unit 301 may be coupled via bus 324 to an integral display 321, possibly a touch-screen display, for use in displaying information to a user. If desired, computing unit 301 may be coupled via bus 324 to an external display screen 344. An external input device 343 (e.g., a standard keyboard) may be coupled to bus 324 for communicating information and command selections to processor 322. A cursor control device 342, such as a mouse, a trackball, or cursor direction keys, may be used for communicating direction information and command selections to processor 322 and for controlling cursor movement on display 344. An external storage device 341 may be connected to the computing unit 301 via bus 324 to provide an extra or removable storage capacity for the computing unit 301, which may be used to facilitate exchange of data with other computer systems.

While the apparatuses and methods of subject invention have been shown and described with reference to preferred embodiments, it is to be understood that any feature described in connection with one embodiment can be advantageously applied to other embodiments of the invention, even if not explicitly described in connection therewith, if such feature(s) are not mutually exclusive with other features of such embodiment. Nevertheless, those skilled in the art will readily appreciate that further changes or modifications may be made to devices and methods of the present invention without departing from the spirit and scope thereof. It is also to be appreciated that the following claims can be rearranged, combined, combined with other features disclosed herein, presented in multiple dependent form and the like.

What is claimed is:

1. A system for mixed reality viewing of a surgical site including viewing of an incision portal for a laparoscopic instrument and an interior body cavity, said system comprising:
    an endoscope having an elongated body with a proximal end and an opposing distal end;
    a spherical element, said spherical element comprising:
        a plurality of cameras, said plurality of cameras being equally distributed about an entirety of said spherical element, each camera including a wide field of view configured to provide video of a field of view portion of the interior body cavity; and
        a fiber optic illumination strip around the periphery of said spherical element positioned adjacent each camera;
    a central processing unit in electronic communication with said plurality of cameras, configured to receive said video in real-time from each of said plurality of cameras;
    a mixed reality headset electronically coupled to said central processing unit, wherein said mixed reality headset is configured to display at least some portion of said video from at least some of said plurality of cameras, said central processing unit configured to adjust said displayed video in real time to correspond to a current spatial orientation of said mixed reality headset with respect to the interior body cavity; and
    a strut, said strut configured to couple said spherical element to said distal end of said endoscope, said strut comprising a lateral extent being less than one-third of a diameter of said spherical element, with said plurality of cameras thereby configured to provide omnidirectional, 360 degree by 360 degree, stereoscopic video capability within the internal body cavity, including the target surgical organ or tissue, portions of the internal body cavity laterally positioned thereto, and the incision portal from within the internal body cavity; and
    wherein said central processing unit is configured to provide said displayed video from any one or more of said plurality of cameras.

2. The system as recited in claim 1 wherein said central processing unit is configured to merge said real-time video from said at least some of said plurality of cameras and remove redundant portions for said display by said mixed reality headset.

3. The system as recited in claim 2,
    wherein said mixed reality headset is angled in the cephalad direction and obstructs only an upper portion of a field of view of a user to permit simultaneous visualization of said real-time video and the incision portal;
    wherein when the user looks upward, said mixed-reality headset provides stereoscopic, virtual reality viewing of the internal body cavity for about 50-70 percent of the user's vertical field of view of both eyes; and
    wherein when the user looks downward, about 30-50 percent of the user's field of view of both eyes visualizes the real-life exterior of the incision portal being unobstructed.

4. The system as recited in claim 3, further comprising a fiber optic illumination strip configured to extend around a periphery of said spherical element.

5. The system as recited in claim 4 wherein said fiber optic illumination strip is configured to extend around said periphery of said spherical element at an equatorial plane.

6. The system as recited in claim 4, wherein said fiber optic illumination strip is configured to extend around said periphery of said spherical element an equatorial plane and about a longitudinal plane.

7. The system as recited in claim 4, further comprising a cable disposed through an internal channel of said endoscope, said cable configured to provide a source of power to said plurality of cameras and a source of light to said fiber optic illumination strip.

8. The system as recited in claim 7, further comprising a secondary processing unit housed at a proximal end of said endoscope and being electronically coupled to said central processing unit, said secondary processing unit configured to initially process said real-time video from each of said plurality of cameras and to provide said processed video to said central processing unit.

9. The system as recited in claim 4, further comprising a light source configured to provide light to said fiber optic illumination strip.

10. The system as recited in claim 9, wherein said endoscope comprises an orientation marker at said proximal end configured to provide a physical representation of said orientation of said plurality of cameras.

11. The system as recited in claim 1, wherein said central processing unit includes a processor operatively connected to a memory, wherein said memory includes instructions recorded thereon that, when read by said processor, cause said processor to:
    receive said real-time video from each of said plurality of cameras;
    receive said current spatial orientation of said headset;
    compare said current spatial orientation of said headset with individual locations of each of said plurality of cameras;
    define a portion of said plurality of cameras which represent a 360 degree view of said spatial orientation of said headset; and
    provide real-time video output from said portion of said cameras that correspond to said spatial orientation of said headset.

12. The system as recited in claim 11,
    wherein said mixed reality headset comprises a gyroscope;

wherein said gyroscope determines a baseline spatial orientation with respect to the interior body cavity; and wherein said gyroscope and said processor are configured to cause said real-time video in said headset to scroll in a direction of movement of said headset, when said mixed-reality headset is moved a threshold amount beyond said baseline spatial orientation.

13. The system as recited in claim 12, wherein said threshold amount comprises movement greater than any one of: five degrees movement laterally, five degrees movement upwardly, and five degrees movement downwardly; and wherein said baseline spatial orientation comprises a line of site directly at a center of the surgical site.

14. The system as recited in claim 11, further comprising: a foot pedal electronically coupled to said secondary processing unit and configured to cause scrolling of said real time video, such that when said foot pedal is moved to the left or to the right, said real time video correspondingly scrolls left or right, and when said foot pedal is moved forward or backward, said real time video correspondingly scrolls up or down.

15. The system as recited in claim 11, further comprising: actuation means electronically coupled to said secondary processing unit for causing scrolling of said real time video, whereby actuating said actuation means to the left or to the right thereby causing correspondingly scrolling of said real time video to the left or right, and whereby actuating said actuation means forward or backward thereby causing correspondingly scrolling up or down of said real time video.

16. The system as recited in claim 1, comprising: a clear sheath configured to enclose said plurality of cameras and at least a portion of said endoscope, and said sheath further configured to provide saline inflow to said spherical element, and saline outflow therefrom.

17. The system as recited in claim 16, wherein said case is autoclavable.

18. The system as recited in claim 1, wherein said elongated body of said endoscope is rigid.

19. The system as recited in claim 1, wherein said elongated body of said endoscope is flexible.

20. A system for mixed reality viewing of an internal surgical site comprising:

an endoscope having an elongated body with a proximal end and an opposing distal end;

a spherical element, said spherical element comprising:

a plurality of wide angle image collection means, said plurality of wide angle image collection means being equally distributed about an entirety of said spherical element, each said wide angle image collection means configured to provide video of a field of view portion of the internal surgical site; and an illumination means positioned adjacent each said wide angle image collection means on said spherical element;

a central processing unit in electronic communication with each said wide angle image collection means, and configured to receive said video in real-time from each said wide angle image collection means;

a mixed reality headset electronically coupled to said central processing unit, wherein said mixed reality headset is configured to display at least some portion of said video from at least some of said plurality of wide angle image collection means, said central processing unit configured to adjust said displayed video in real time to correspond to a current spatial orientation of said mixed reality headset with respect to the internal surgical site;

an optical tube, said optical tube configured to couple said spherical element to said distal end of said endoscope, said optical tube comprising a smaller lateral extent than said endoscope, with said plurality of wide angle image collection means thereby configured to provide omnidirectional, 360 degree by 360 degree, stereoscopic video capability, with said central processing unit being configured to provide said displayed video from any one or more of said plurality of wide angle image collection means.

* * * * *